(12) United States Patent
Hashimoto

(10) Patent No.: US 12,239,590 B2
(45) Date of Patent: Mar. 4, 2025

(54) NURSING BED SYSTEM AND NURSING BED POSTURE CHANGING DEVICE

(71) Applicant: Kawasaki Jukogyo Kabushiki Kaisha, Kobe (JP)

(72) Inventor: Yasuhiko Hashimoto, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 485 days.

(21) Appl. No.: 17/739,207

(22) Filed: May 9, 2022

(65) Prior Publication Data

US 2022/0257441 A1 Aug. 18, 2022

Related U.S. Application Data

(63) Continuation of application No. PCT/JP2020/041592, filed on Nov. 6, 2020.

(30) Foreign Application Priority Data

Nov. 7, 2019 (JP) ................................. 2019-202765

(51) Int. Cl.
*A61G 7/015* (2006.01)
*A61B 5/00* (2006.01)
*A61G 7/018* (2006.01)
*G06N 20/00* (2019.01)

(52) U.S. Cl.
CPC .............. *A61G 7/015* (2013.01); *A61B 5/749* (2013.01); *A61G 7/018* (2013.01); *G06N 20/00* (2019.01)

(58) Field of Classification Search
CPC ......... A61G 7/018; A61G 7/005; A61G 7/015
See application file for complete search history.

(56) References Cited

U.S. PATENT DOCUMENTS

| | | | |
|---|---|---|---|
| 10,092,468 B2 | 10/2018 | Hashimoto | |
| 12,127,982 B2* | 10/2024 | Clayton | A47B 9/20 |
| 2002/0014951 A1* | 2/2002 | Kramer | G16H 10/60 340/286.07 |
| 2005/0160530 A1* | 7/2005 | Taguchi | A61G 7/001 5/613 |
| 2014/0169795 A1* | 6/2014 | Clough | H04W 88/02 398/106 |
| 2017/0007480 A1 | 1/2017 | Koch | |
| 2018/0161225 A1* | 6/2018 | Zerhusen | A61G 7/05769 |
| 2019/0116986 A1 | 4/2019 | Werner | |
| 2019/0192364 A1* | 6/2019 | Upchurch | A61G 7/08 |

FOREIGN PATENT DOCUMENTS

| | | |
|---|---|---|
| CN | 109646215 A | 4/2019 |
| JP | 6345119 B2 | 6/2018 |
| WO | 2013/123119 A1 | 8/2013 |

* cited by examiner

*Primary Examiner* — Eric J Kurilla
(74) *Attorney, Agent, or Firm* — XSENSUS LLP (57) ABSTRACT

A nursing bed system includes a nursing bed and a nursing bed posture changing device. The nursing bed posture changing device includes care recipient data acquiring circuitry that acquires care recipient data containing at least one of voice data of a care recipient who lies on the nursing bed, and image data obtained by imaging the care recipient, bed posture information generating circuitry that generates bed posture mode information according to a demand by the care recipient based on the care recipient data, and posture changing circuitry that changes the posture of the nursing bed based on the bed posture mode information.

14 Claims, 4 Drawing Sheets

NURSING BED SYSTEM AND NURSING BED POSTURE CHANGING DEVICE

CROSS-REFERENCE TO RELATED APPLICATIONS

The present application is a Continuation of PCT International Application No. PCT/JP2020/041592, filed on Nov. 6, 2020, which claims priority to JP 2019-202765, filed on Nov. 7, 2019, the entire contents of each are incorporated herein by reference.

TECHNICAL FIELD

The present disclosure relates to a nursing bed system and a nursing bed posture changing device.

BACKGROUND ART

At nursing sites, a care worker changes the posture of a care recipient so that the care recipient who lies on a nursing bed takes the easiest posture for himself/herself. Such a care worker's work is hard work because he/she supports the care recipient's weight and it is necessary to carry out all day and night, and the burden is large for the care worker. Thus, devices which automatically change the posture of the care recipient who lies on the nursing bed are proposed. For example, a nursing bed disclosed in Patent Document 1 is provided with an upper surface forming member which forms a bed surface (upper surface) where the care recipient lies, and a drive mechanism which moves at least a part of the upper surface forming member. The bed surface includes a curved surface which curves downwardly in the width direction of the nursing bed, and a rotation driving force is transmitted to the drive mechanism from a rotary driver attached to a tip-end part of a robotic arm. The robotic arm automatically performs given operation for suppressing bedsore by executing a program incorporated into a control unit beforehand.

REFERENCE DOCUMENT OF CONVENTIONAL ART

Patent Document

[Patent Document 1] JP6345119B2

DESCRIPTION OF THE DISCLOSURE

Problem(s) to be Solved by the Disclosure

However, depending on the body size and the condition (e.g., the disease) of the care recipient, this bedsore operation may give the care recipient displeasure and pain. Therefore, although the conventional nursing bed described above is configured to be changeable of the contents of the program according to the care recipient, this changing work may become the burden for the care worker. Further, although watching the care recipient all day long by the care worker is preferred, the burden is large for the care worker.

The present disclosure is made in order to solve the above problems, and one purpose thereof is to provide a nursing bed which can ease the care worker's burden.

Means for Solving the Problem(s)

In order to achieve the purpose, a nursing bed posture changing device according to one aspect of the present disclosure is a device that changes a posture of a nursing bed, the nursing bed being changeable of the shape of a floor of the bed, and/or a posture related to an angle of the entire bed. The device includes care recipient data acquiring circuitry that acquires care recipient data containing at least one of voice data of a care recipient who lies on the nursing bed, and image data obtained by imaging the care recipient, bed posture information generating circuitry that generates bed posture mode information according to a demand by the care recipient based on the care recipient data, and posture changing circuitry that changes the posture of the nursing bed based on the bed posture mode information.

Further, a nursing bed system according to one aspect of the present disclosure includes a nursing bed changeable of the shape of a floor of the bed, and/or a posture related to an angle of the entire bed, and the nursing bed posture changing device described above.

Effect of the Disclosure

Since the present disclosure has the configurations described above, according to the present disclosure, a nursing bed which can ease the care worker's burden can be provided.

MODES FOR CARRYING OUT THE DISCLOSURE

Hereinafter, desirable embodiments are described with reference to the drawings. Note that, below, the same reference characters are assigned to the same or corresponding elements throughout the drawings to omit redundant explanation. Further, the drawings illustrate each component schematically for easier understandings.

First Embodiment

Figure 1:
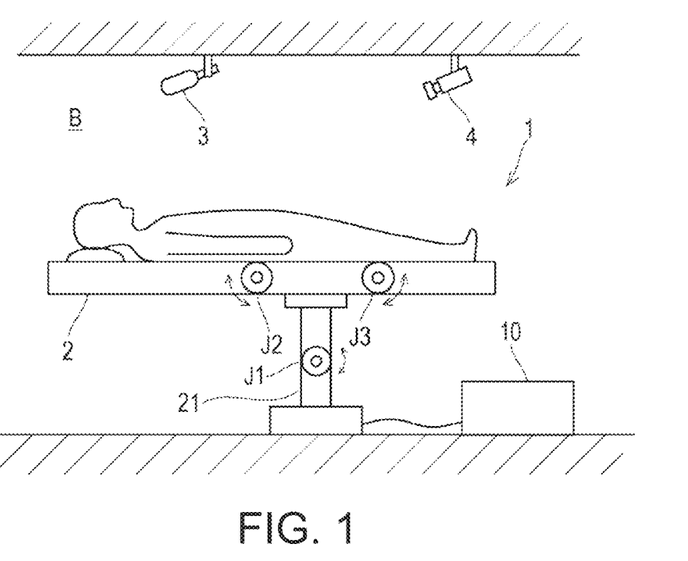
FIG. 1 is a view of a nursing bed system according to a first embodiment of the present disclosure.

FIG. 1 is a view of a nursing bed system 1 according to a first embodiment of the present disclosure. As illustrated in FIG. 1, the nursing bed system 1 includes a nursing bed 2, and a nursing bed posture changing device (hereinafter, may simply be referred to as "the posture changing device").

The nursing bed 2 is provided with three joints so that the shape of a floor of the bed, and/or the posture related to the angle of the entire bed are changeable. The floor of the nursing bed 2 is formed in a flat plate shape. The floor of the nursing bed 2 is divided in the longitudinal direction into an upper body area, a waist area, and a leg area. The floor (waist area) of the nursing bed 2 is supported by a base part attached at a tip end of a robotic arm 21. Further, the base end of the robotic arm 21 is fixed to a floor of a care room B. The robotic arm 21 has one joint (first joint J1), and the angle of the entire bed is changed by being driven by a motor which is established in the first joint J1. Two joints (second joint J2, third joint J3) are provided to the floor of the nursing bed 2. The second joint J2 is provided to a connecting part between the upper body area and the waist area. By being driven by a motor established in the second joint J2, the angle of the upper body area with respect to the waist area (elevation angle) is changed. The third joint J3 is provided to a connecting part between the waist area and the leg area. By being driven by a motor established in the third joint J3, the angle of the leg area with respect to the waist area (elevation angle) is changed. Therefore, the shape of the floor of the nursing bed 2 can be changed. Note that, although the change in the shape of the floor of the nursing bed 2 is made by the drive of the motors established in the joints J2 and J3 provided to the floor of the nursing bed 2, the joints J2 and J3 may be configured to be external shafts of the robotic arm 21.

A microphone 3 and a camera 4 are installed in the ceiling of the care room B. The microphone 3 acquires voice of a care recipient. The camera 4 images a situation of the care recipient. The microphone 3 and the camera 4 are communicatably connected to the posture changing device 10, and the voice data of the microphone 3 and the image data of the camera 4 are inputted into the posture changing device 10.

Figure 2:
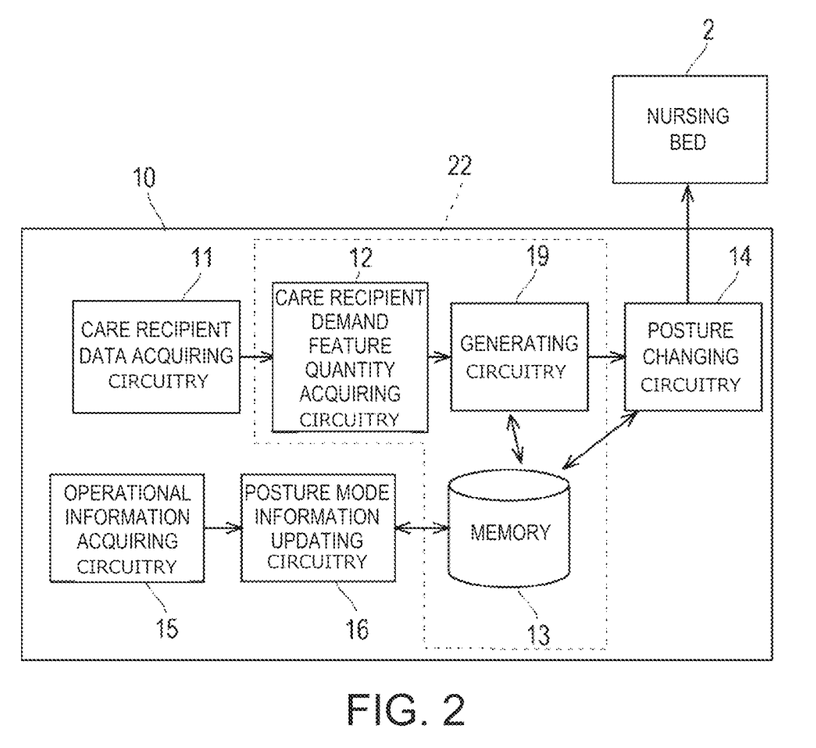
FIG. 2 is a functional block diagram schematically illustrating a configuration of a nursing bed posture changing device.

FIG. 2 is a functional block diagram schematically illustrating a configuration of the posture changing device 10. As illustrated in FIG. 2, the posture changing device 10 includes care recipient data acquiring circuitry 11, bed posture information generating circuitry 22 (the bed posture information generating circuitry 22 includes care recipient demand feature quantity extracting circuitry 12, a memory 13, and generating circuitry 19), posture changing circuitry 14, operational information acquiring circuitry 15, and bed posture mode information updating circuitry 16. The posture changing device is a robot controller provided with a computer, such as a microcontroller, for example. The memory 13 stores information on a basic program as a robot controller, various fixed data, etc. By an arithmetic unit executing software, such as the basic program stored in the memory 13, each part of the posture changing device 10 is operated.

The care recipient data acquiring circuitry 11 acquires care recipient data. The care recipient data includes at least one of voice data of the care recipient who lies on the nursing bed 2, the image data obtained by imaging the care recipient, and the time data. In this embodiment, the care recipient data acquiring circuitry 11 acquires the voice data of the microphone 3 and the time data.

The care recipient demand feature quantity extracting circuitry 12 extracts a demand feature quantity by which a care recipient's demand is characterized, based on at least one of the care recipient's voice data, the care recipient's image data, and the time data acquired by the care recipient data acquiring circuitry 11. In this embodiment, the care recipient demand feature quantity extracting circuitry 12 extracts a demand feature quantity by which a care recipient's demand by an utterance "Get me up" is characterized, based on the care recipient's voice data and the time data which are acquired by the care recipient data acquiring circuitry 11.

The memory 13 stores beforehand bed posture mode information for identifying the posture of the nursing bed 2 associated with a specific demand from the care recipient. In this embodiment, the memory 13 stores bed posture mode information on the nursing bed 2 associated with the specific demand by the care recipient's utterance "Get me up." Here, the bed posture mode information is information on the joint angles (rotational positions) of the three joints J1-J3 of the nursing bed 2. For example, the bed posture mode information is information on the angles of the first joint J1 and the third joint J3 being maintained at 0°, and the angle of the second joint J2 being rotated 30° in the clockwise direction.

The generating circuitry 19 reads, from the memory 13, the bed posture mode information associated with the specific demand which matches with the care recipient's demand extracted by the care recipient demand feature quantity extracting circuitry 12, and uses it as the bed posture mode information generated by the bed posture information generating circuitry 22. The posture changing circuitry 14 changes the posture of the nursing bed 2 based on the generated bed posture mode information. In this embodiment, based on the bed posture mode information on the nursing bed 2 associated with the specific demand by the care recipient's utterance "Get me up," driving commands of the motors of the joints J1-J3 are generated to change the posture of the nursing bed 2.

The operational information acquiring circuitry 15 acquires operational information operated by a care worker. In this embodiment, a remote controller for user interface (not illustrated) installed by the nursing bed 2 is communicatably connected to the posture changing device 10 wirelessly or wiredly, and the operational information on the remote controller for user interface is inputted into the posture changing device 10 (operational information acquiring circuitry 15).

The bed posture mode information updating circuitry 16 updates the contents of the bed posture mode information stored in the memory 13 according to the operational information acquired by the operational information acquiring circuitry 15. For example, the bed posture mode information updating circuitry 16 updates the contents of the bed posture mode information among the bed posture mode information on the nursing bed 2 associated with the specific demand by the care recipient's utterance "Get me up" according to the operational information acquired by the operational information acquiring circuitry 15 so that a rotational amount of the angle of the second joint J2 is incremented by 1°.

Figure 3:
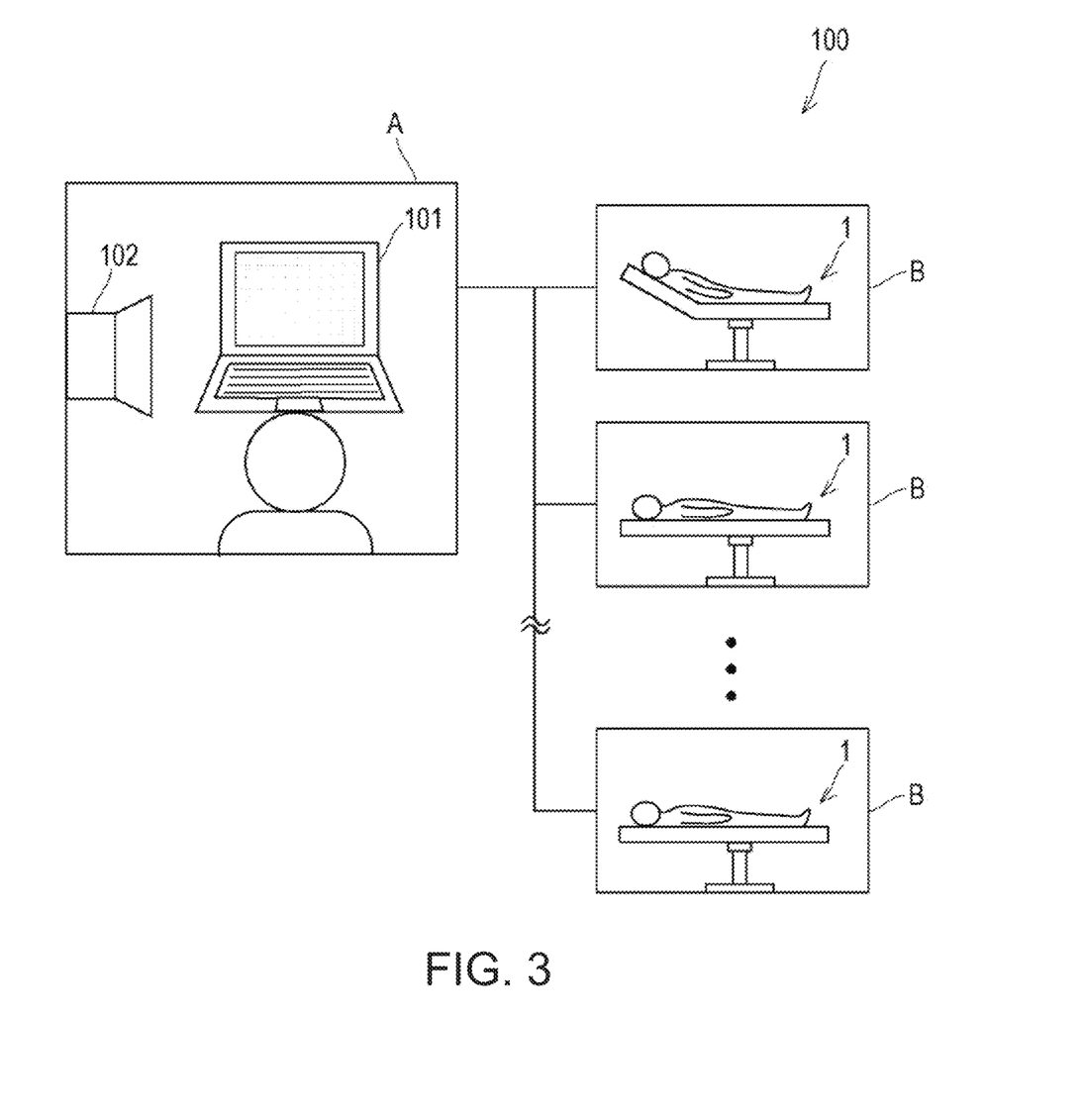
FIG. 3 is a view illustrating one example of a nursing home to which the nursing bed system is applied.

FIG. 3 is a view illustrating one example of a nursing home 100 to which the nursing bed system 1 of FIG. 1 is applied. As illustrated in FIG. 3, the nursing home 100 includes a management office A and a plurality of care rooms B. Note that the nursing bed system 1 described above is applied to each care room B. A managing device 101 and a speaker 102 are installed in the management office A. The managing device 101 is connected to the camera 4 (see FIG. 1) of each care room B so that the situation of the care recipient in the care room B is projected on a monitor of the managing device 101. The managing device 101 is a personal computer, for example. The speaker 102 of the management office A is connected to the microphone 3 (see FIG. 1) of each care room B so that an administrator in the management office A is able to have a conversation with the care recipient in the care room B.

Next, operation of the nursing bed system 1 of this embodiment is described. First, when the care recipient (bed user) in the care room B says "Get me up," the posture of the nursing bed 2 is changed so that the care recipient can rise his/her upper body in a comfortable posture.

When the care recipient is not satisfied with the shape of the floor of the nursing bed 2, or the angle of the bed, he/she contacts the administrator in the management office A. The administrator who received the complaint comes into the care room B and operates the remote controller for user interface to change the shape of the floor and the angle of the bed to the care recipient's favorite shape and angle. The administrator may change the posture of the nursing bed 2 by remote control from the management office A. The nursing bed system 1 updates the bed posture mode information in the memory 13, and whenever the care recipient says "Get me up" thereafter, the updated posture of the nursing bed 2 will be reproduced.

As described above, the nursing bed system 1 of this embodiment includes the nursing bed 2 configured to be changeable of the shape of the floor of the bed, and/or the posture related to the angle of the entire bed, the care recipient data acquiring circuitry 11 which acquires at least one of the voice data of the care recipient who lies on the nursing bed 2, the image data obtained by imaging the care recipient, and the time data, the care recipient demand feature quantity extracting circuitry 12 which extracts the demand feature quantity by which the care recipient's demand is characterized based on at least one of the care recipient's voice data, the care recipient's image data, and the time data acquired by the care recipient data acquiring circuitry 11, the memory 13 which stores beforehand the bed posture mode information for identifying the posture of the nursing bed 2 associated with the specific care recipient's demand, the posture changing circuitry 14 which changes the posture of the nursing bed 2 based on the bed posture mode information associated with the specific demand which matches with the care recipient's demand extracted by the care recipient demand feature quantity extracting circuitry 12, the operational information acquiring circuitry 15 which acquires the operational information operated by the care worker, and the bed posture mode information updating circuitry 16 which updates the bed posture mode information according to the operational information acquired by the operational information acquiring circuitry 15.

According to the nursing bed system 1 of this embodiment, if the care worker once adjusts the posture of the nursing bed 2 to become suitable for the care recipient, since the care worker will never need to perform the adjustment again, the care worker's burden can be eased.

Note that, although in this embodiment the care recipient's demand is the verbal demand, it may be a demand by gesture. In that case, in the posture changing device 10 of FIG. 2, the care recipient data acquiring circuitry 11 acquires the image data of the camera 4. Further, the care recipient demand feature quantity extracting circuitry 12 extracts the demand feature quantity by which a demand by a gesture of "Trying to rise the upper body" is characterized, from the care recipient's image data based on the care recipient's image data acquired by the care recipient data acquiring circuitry 11. The memory 13 stores the bed posture mode information on the nursing bed 2 associated with the specific demand by the gesture "Trying to rise the upper body" of the care recipient.

Note that the demand by the gesture is not limited to a demand which is consciously performed by the care recipient, but it may be a demand which is unconsciously performed by the care recipient, for example, like a body motion during sleep. For example, when the care recipient rises a knee during sleep, the floor of the nursing bed 2 may be deformed so that the care recipient's legs are lifted.

Although in this embodiment one managing device 101 is connected with the plurality of nursing bed systems 1, a plurality of management offices A may be provided to the nursing home 100 and a plurality of managing devices 101 may be connected with the plurality of nursing bed systems 1.

Further, the posture changing device 10 may be provided with an alarm function which changes the angle of the floor of the nursing bed 2 to raise the care recipient's upper body in response to an utterance demand of the care recipient who says "Wake me up" at a given time (for example, 7 o'clock in the morning).

Second Embodiment

Figure 4:
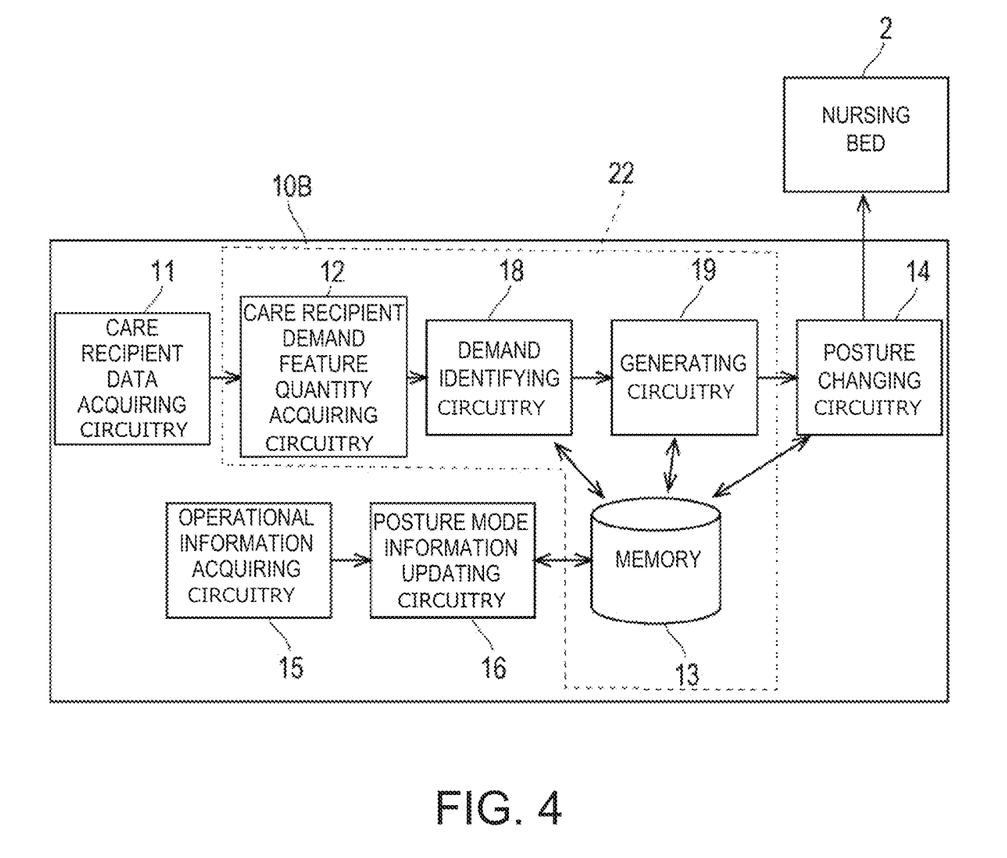
FIG. 4 is a block diagram illustrating a configuration of a nursing bed posture changing device provided to a nursing bed system according to a second embodiment of the present disclosure.

Next, a nursing bed system 1 according to a second embodiment of the present disclosure is described. FIG. 4 is a functional block diagram schematically illustrating a configuration of a posture changing device 10B of the nursing bed 2 according to the second embodiment. The nursing bed system 1 according to the second embodiment includes the nursing bed 2 and the posture changing device 10B. Since the configuration of the nursing bed 2 according to the second embodiment is similar to the configuration of the first embodiment (see FIG. 1), explanation thereof is omitted.

As illustrated in FIG. 4, the posture changing device 10B includes the care recipient data acquiring circuitry 11, the bed posture information generating circuitry 22, the memory 13, the posture changing circuitry 14, the operational information acquiring circuitry 15, and the bed posture mode information updating circuitry 16. The bed posture information generating circuitry 22 includes the care recipient demand feature quantity extracting circuitry 12, a demand identifying circuitry 18, and the generating circuitry 19. The posture changing device 10B is a robot controller provided with a computer, such as a microcontroller, for example. The memory 13 stores information on the basic program as the robot controller, various fixed data, etc. By an arithmetic unit executing the software, such as the basic program stored in the memory 13, operation of each function part of the posture changing device 10B is performed.

The care recipient data acquiring circuitry 11 acquires at least one of the voice data of the care recipient who lies on the nursing bed 2, and the image data obtained by imaging the care recipient. The voice data is comprised of sound measured by the microphone 3. The image data is comprised of image captured by the camera 4. The care recipient data acquiring circuitry 11 may be configured to acquire, in addition to the voice data and image data, time data indicative of the time when the data are generated.

The care recipient demand feature quantity extracting circuitry 12 extracts the demand feature quantity by which the care recipient's demand is characterized based on at least one of the voice data and the image data acquired by the care recipient data acquiring circuitry 11. For example, the voice data acquired by the microphone 3 is comprised of sounds which are put in the time-series order. The care recipient demand feature quantity extracting circuitry 12 extracts the care recipient's voice by removing noise such as machinery sound from the voice data, and the extracted voice is converted into text or a signal by using a speech recognition technology to become the demand feature quantity. Further, for example, a part or all of the care recipient's body is projected on the image data acquired by the camera 4. The care recipient demand feature quantity extracting circuitry 12 extracts, from this image data, the demand feature quantity for deriving the care recipient's demand from the care recipient's gesture (motion). The demand feature quantity in this case may be information indicative of the overall or partial motion and its amount of the care recipient's body, such as a moving amount of the care recipient's hand, a moving amount of the leg, a moving amount of the head, and the motion of the mouth or the eyes, for example.

The demand identifying circuitry 18 acquires the demand feature quantity generated by the care recipient demand feature quantity extracting circuitry 12, and identifies (estimates) the care recipient's demand based on the demand feature quantity. The voice uttered by the care recipient may not be a perfect language, such as "Ah" or "Oh," or may be only a word. Moreover, the voice uttered by the care recipient may be a foreign language or a dialect. The care recipient's gesture is peculiar to the care recipient, and may be different for different care recipients. The demand identifying circuitry 18 identifies the care recipient's demand from the demand feature quantity based on a specific rule stored beforehand. The specific rule is information for associating the demand feature quantity with the care recipient's demand. The specific rule may be created for every care recipient. Upon identifying the care recipient's demand based on the demand feature quantity, the demand identifying circuitry 18 may additionally use the time data which is obtained when the demand feature quantity is generated. That is, the demand identifying circuitry 18 can identify (estimate) the care recipient's demand based on a combination of the demand feature quantity and the time data. By combining the demand feature quantity and the time data, it can more accurately identify the care recipient's demand.

The memory 13 stores a plurality of kinds of demands of the care recipient, and bed posture mode information which is associated with each of the plurality of kinds of demands. The bed posture mode information is information for identifying the posture of the nursing bed 2. Here, since the posture of the nursing bed 2 is defined by the angles of the three joints J-J3, the bed posture mode information is information on the angles of the three joints J1-J3 of the nursing bed 2. For example, the memory 13 stores the bed posture mode information on the nursing bed 2 associated with the care recipient's demand "Get me up."

The generating circuitry 19 reads, from the memory 13, the bed posture mode information associated with the specific demand which matches with the care recipient's demand extracted by the care recipient demand feature quantity extracting circuitry 12, and uses it as the bed posture mode information generated by the bed posture information generating circuitry 22.

The posture changing circuitry 14 changes the posture of the nursing bed 2 based on the generated bed posture mode information. For example, based on the bed posture mode information on the nursing bed 2 associated with the care recipient's demand "Get me up," the posture changing circuitry 14 generates the driving command of the motors of the joints J1-J3, and changes the posture of the nursing bed 2.

The care recipient contacts the administrator in the management office A, if he/she is neither satisfied with the shape of the floor of the nursing bed 2, nor the angle of the bed. The administrator who received the complaint operates the remote controller for user interface in the care room B or in the management office A to change the shape of the floor and the angle of the bed as the care recipient prefers. The command is inputted into the posture changing device 10 via the remote controller for user interface, and the posture of the nursing bed 2 is adjusted. The nursing bed system 1 acquires a state, such as the posture of the nursing bed 2, which is updated by the care worker, and updates the bed posture mode information stored in the memory 13 corresponding to the specified demand described above. The state, such as the posture of the nursing bed 2, can be identified based on the rotational positions of the joints J1-J3, the information captured by the camera 4, etc. Thus, by sequentially updating the bed posture mode information, the updated posture of the nursing bed 2 is reproduced when a similar demand is issued next. Therefore, the posture of the nursing bed 2 can be changed not only according to the care recipient's preference but also according to the change in the care recipient's body state.

Third Embodiment

Figure 5:
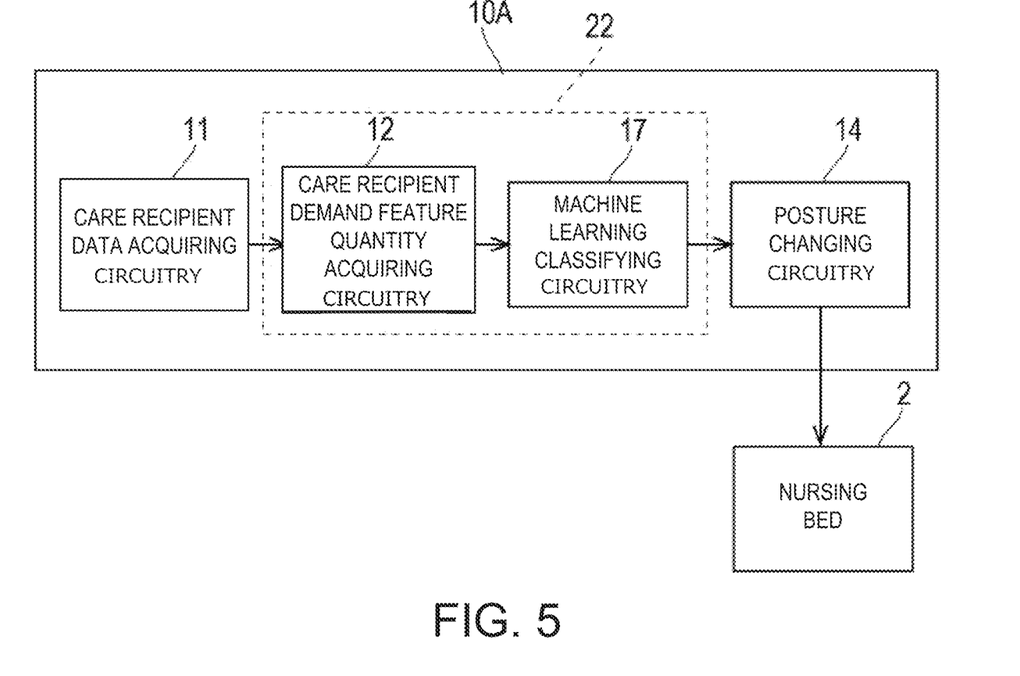
FIG. 5 is a block diagram illustrating a configuration of a nursing bed posture changing device provided to a nursing bed system according to a third embodiment of the present disclosure.

Next, a posture changing device 10A of the nursing bed 2 of a third embodiment of the present disclosure is described with reference to a block diagram of FIG. 5. Note that, since a configuration of the nursing bed 2 is similar to the configuration (see FIG. 1) of the first embodiment, explanation thereof is omitted. As illustrated in FIG. 5, the posture changing device 10A includes the care recipient data acquiring circuitry 11, the bed posture information generating circuitry 22 which is mainly comprised of a machine learning classifying circuitry 17, and the posture changing circuitry 14. Since the care recipient data acquiring circuitry 11 and the posture changing circuitry 14 of the posture changing device 10A have the same or similar configuration as/to those of the posture changing device 10 of the first embodiment, explanation thereof is omitted. The posture changing device 10A differs from the posture changing device 10 of FIG. 1 in that it is mainly provided with the machine learning classifying circuitry 17 instead of the memory 13, the operational information acquiring circuitry 15, and the bed posture mode information updating circuitry 16.

The machine learning classifying circuitry 17 is established with a plurality of teaching data in which the demand feature quantity for learning by which the care recipient data or the care recipient's demand is characterized is associated with the bed posture mode information for identifying the posture of the nursing bed 2 (the bed posture mode information as a correct answer). The machine learning classifying circuitry 17 is generated by a machine learning device 30 having an AI function as illustrated in a block diagram of FIG. 6. The machine learning device 30 includes teaching data acquiring circuitry 31 which acquires a plurality of teaching data, machine learning circuitry 32 which establishes a classifying circuitry of the machine learning by using the teaching data, and machine learning classifying circuitry outputting circuitry (classifying circuitry information outputting circuitry) 33 which outputs the information on the established machine learning classifying circuitry 17.

The care recipient data acquired by the care recipient data acquiring circuitry 11 or its processed data is inputted into the machine learning classifying circuitry 17, and the bed posture mode information is outputted from the machine learning classifying circuitry 17. The processed data of the care recipient data includes the demand feature quantity generated based on at least one of the care recipient's voice data and the care recipient's image data (refer to the explanation of the first embodiment and the second embodiment). The posture changing circuitry 14 changes the posture of the nursing bed 2 based on the bed posture mode information outputted from the machine learning classifying circuitry 17.

First, the care worker (person) changes the shape and the angle of the bed according to the care recipient's demand and time. Although the care recipient's demand is the demand by the care recipient's utterance, it may be the demand by the care recipient's gesture, for example. The care worker recognizes the care recipient's demand and the time at that time, and then adjusts the shape and the angle of the bed so that the care recipient becomes in a comfortable posture.

The care recipient's demand is converted into numerical data (demand data). Time at that time is also converted into numerical data (time data). The adjustment performed by the care worker according to the care recipient's demand data and the time data is also converted into numerical data (adjustment data). The care recipient's utterance can be acquired by the microphone 3, and can be converted into the voice data. If the level of the sound inputted into the microphone 3 exceeds a threshold, voice data is then acquired from this timing for a fixed period of time (for example, 2 seconds), and it is converted into the voice data for learning. Further, the care recipient's gesture may be imaged by the camera 4, and may be converted into the image data. If a change per time in the image captured by the camera 4 exceeds a threshold, it is considered to be a demand by gesture, and the image data is then acquired from this timing for a fixed period of time (for example, 3 seconds), and it is converted into the image data for learning. The angle data of the joint J1 of the robotic arm 21, and the angle data of the joints J2 and J3 of the floor of the bed, which are adjusted by the care worker, can be used as adjustment data for learning. By recording raw data set including the time, the demand from the care recipient, and the adjustment of the bed for every specific demand (adjustment by the care worker), over a long period of time, teaching data for learning of the machine learning (multi-class classification) in which the time data, the demand data, and the adjustment data corresponding to these data are grouped can be created. The teaching data may be data obtained by preprocessing the raw data set.

Figure 6:
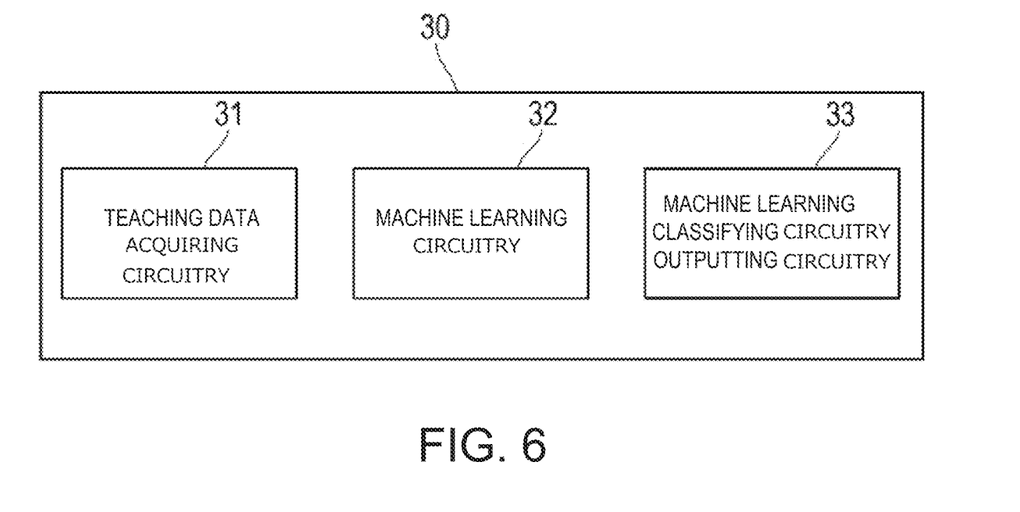
FIG. 6 is a block diagram illustrating a configuration of a machine learning device which generates machine learning classifying circuitry of FIG. 5.

The machine learning device 30 acquires a large number of teaching data for learning by the teaching data acquiring circuitry 31, and carries out the machine learning by the machine learning circuitry 32. Each of the large number of teaching data includes a combination of input data containing the care recipient data (or its processed data) and output data containing the bed posture mode information according to the care recipient's demand, which is associated with the input data. The input data as the teaching data is generated from the time data and the demand data described above. The output data as the teaching data is generated from the adjustment data described above. The machine learning circuitry 32 identifies the feature which suggests the correlation between the input data and the output data based on the teaching data by using the given learning algorithm to learn a correlation model for estimating output data necessary for new input data. This correlation model becomes the learned model. The machine learning classifying circuitry outputting circuitry 33 outputs the thus-obtained learned model to the machine learning classifying circuitry 17. The machine learning classifying circuitry 17 derives the bed posture mode information as the output data from the care recipient data (or its processed data) as the input data by using the learned model, and outputs what kind of adjustment should be made according to the care recipient's demand to the posture changing circuitry 14. The posture changing circuitry 14 changes the joint angle of the floor and the joint angle of the robotic arm 21 according to the output.

If the adjustment (bed posture mode information) derived by the machine learning classifying circuitry 17 is satisfactory for the care recipient, the care recipient does not need to notify the administrator. The image data etc. at that time and the output value of the machine learning classifying circuitry 17 are saved as the next teaching data for learning. On the other hand, if the adjustment made by the machine learning classifying circuitry 17 is not satisfactory for the care recipient, the care recipient notifies the administrator. Then, the administrator corrects the bed to the correct shape and angle. Then, a set of the image data etc. at that time and the corrected data of the shape and the angle are saved as the next teaching data for learning.

Thus, when a set or a plurality of sets of new teaching data for learning are saved, a new data set for learning to which the teaching data are added is created, and the machine learning using the new data set is performed.

As described above, the nursing bed posture changing device 10A according to this embodiment includes the care recipient data acquiring circuitry 11 which acquires at least one of the care recipient's voice data, the care recipient's image data, and the time data, which are generated by measuring the care recipient's voice or image, and the posture changing circuitry 14 which inputs the care recipient demand feature quantity generated based on at least one of the care worker's voice data, the care recipient's image data, and the time data, which are acquired, to the classifying circuitry 17 of the machine learning which is established with a plurality of teaching data in which the care recipient demand feature quantity for learning by which the care recipient's demand is characterized is associated with the bed posture mode information for identifying the posture of the nursing bed 2 which is the bed posture mode information as a correct answer corresponding to the care recipient demand feature quantity, and changes the posture of the nursing bed 2 based on the outputted bed posture mode information. The machine learning device 30 which generates the information on the classifying circuitry 17 used in the nursing bed posture changing device 10A includes the teaching data acquiring circuitry 31 which acquires a plurality of teaching data in which the care recipient demand feature quantity for learning is associated with the bed posture mode information as a correct answer corresponding to the care recipient demand feature quantity, and the machine learning circuitry 32 which establishes the classifying circuitry 17 of the machine learning with the teaching data, and the classifying circuitry information outputting circuitry (machine learning classifying circuitry outputting circuitry 33) which outputs the information on the established classifying circuitry 17.

According to this embodiment, actual nursing is performed using the machine learning classifying circuitry 17 which becomes "learned" after it once learned. While changing and correcting the posture of the bed, the posture change data (including the corrected data) of the bed is also saved as the new correct answer data for the next machine learning. It is added to the data set for the machine learning used for the previous machine learning, and a further machine learning can be carried out to strengthen the performance of the machine learning classifying circuitry 17.

SUMMARY

As described above, the nursing bed system 1 according to the first to third embodiments is provided with the nursing bed 2 configured to be changeable of the shape of the floor of the bed, and/or the posture related to the angle of the entire bed, and the nursing bed posture changing device 10, 10A, or 10B. The nursing bed system 1 may be further provided with at least one of the microphone 3 which generates the voice data and the camera 4 which generates the image data.

The nursing bed posture changing device 10, 10A, or 10B of the nursing bed system 1 according to the first to third embodiments is the device which changes the posture of the nursing bed 2 configured to be changeable of the shape of the floor of the bed, and/or the posture related to the angle of the entire bed. The device includes the care recipient data acquiring circuitry 11 which acquires the care recipient data containing at least one of the voice data of the care recipient who lies on the nursing bed 2, and the image data obtained by imaging the care recipient, the bed posture information generating circuitry 22 which generates the bed posture mode information according to the care recipient's demand based on the care recipient data, and the posture changing circuitry 14 which changes the posture of the nursing bed 2 based on the bed posture mode information.

According to the nursing bed system 1 and the nursing bed posture changing devices 10, 10A, and 10B, which have the configurations described above, the bed posture mode information according to the care recipient's demand is generated based on the demand (or its sign) issued by the care recipient, and the nursing bed 2 is operated based on the bed posture mode information. Therefore, the bed moves automatically corresponding to the care recipient's demand, and the care recipient's posture may be changed so that it is comfortable for the care recipient. Therefore, it is possible to ease the burden of the care worker for adjusting the care recipient's posture.

In the nursing bed posture changing devices 10 and 10B of the nursing bed system 1 according to the first embodiment and the second embodiment, the bed posture information generating circuitry 22 includes the care recipient demand feature quantity extracting circuitry 12 which extracts the demand feature quantity by which the care recipient's demand is characterized from the care recipient data, the memory 13 which stores the plurality of kinds of demands of the care recipient, and the bed posture mode information for identifying the posture of the nursing bed associated with each of the plurality of kinds of demands, and the generating circuitry 19 which reads, from the memory 13, the bed posture mode information associated with the care recipient's demand corresponding to the demand feature quantity extracted by the care recipient demand feature quantity extracting circuitry.

Further, as described in the second embodiment, the bed posture information generating circuitry 22 may be further provided with the demand identifying circuitry 18 which identifies the care recipient's demand based on the given specific rule based on the demand feature quantity. Therefore, the care recipient's demand can be identified for the demand feature quantities of various modes.

Further, as described in the second embodiment, the care recipient data may further include the time data indicative of the time at which at least one data of the voice data and the image data is generated. The demand identifying circuitry 18 may identify the care recipient's demand based on the demand feature quantity and the time data corresponding thereto. Therefore, the accuracy of identifying the care recipient's demand by the demand identifying circuitry 18 can be improved.

Further, as described in the first and second embodiments, the nursing bed system 1 may further include the operational information acquiring circuitry 15 which acquires the operational information when the posture of the nursing bed 2 is operated by the care worker corresponding to the care recipient's demand, and the bed posture mode information updating circuitry 16 which updates the bed posture mode information which is stored in the memory 13 while being associated with the demand, according to the operational information acquired by the operational information acquiring circuitry 15. Therefore, since the bed posture mode information updating circuitry 16 is sequentially updated by the new information, the comfortable bed posture mode can be provided to the care recipient, even if the care recipient's physical situation is changed.

In the nursing bed posture changing device 10A of the nursing bed system 1 according to the third embodiment, the bed posture information generating circuitry 22 includes the machine learning classifying circuitry 17 which has the learned model learned with the large number of teaching data in which the input data containing the care recipient data or its processed data is associated with the output data containing the bed posture mode information according to the care recipient's demand, and derives the output data corresponding to the input data to be recognized using the learned model. The input data may contain the demand feature quantity by which the care recipient's demand extracted from the care recipient data is characterized. Thus, by using the machine learning classifying circuitry 17 which includes the learned model as the bed posture information generating circuitry 22, the bed posture mode information according to the care recipient's demand can be derived from the care recipient data (or its processed data) with high precision.

As described in the third embodiment, the nursing bed posture changing device 10A may further include the teaching data acquiring circuitry 31 which acquires the large number of teaching data, each comprised of a combination of the input data containing the care recipient data or its processed data, and the output data containing the bed posture mode information according to the care recipient's demand as the correct answer to the input data, and the machine learning circuitry 32 which establishes the machine learning classifying circuitry 17 which associates the input data with the output data by using the large number of teaching data. Therefore, the machine learning classifying circuitry 17 is sequentially learned.

OTHER EMBODIMENTS

Note that, although in the above embodiments, the nursing bed 2 is provided with the three joints (see FIG. 1), it is not limited to this configuration, as long as the nursing bed 2 is provided with one or more joints, and is configured to be changeable of the shape of the floor of the bed, and/or the posture related to the angle of the entire bed. The nursing bed 2 may have the configuration disclosed in FIG. 1 of Patent Document 1, for example.

It is apparent for the person skilled in the art that many improvements and other embodiments of the present disclosure are possible from the above description. Therefore, the above description is to be interpreted only as illustration, and it is provided in order to teach the person skilled in the art the best mode that implements the present disclosure. The details of the structures and/or the functions may be changed substantially, without departing from the spirit of the present disclosure.

INDUSTRIAL APPLICABILITY

The present disclosure is useful at the nursing site, such as the nursing home.

The invention claimed is:

1. A nursing bed posture changing device that changes a posture of a nursing bed, the nursing bed being changeable of the shape of a floor of the bed, and/or a posture related to an angle of the entire bed, the device comprising:
care recipient data acquiring circuitry that acquires care recipient data containing at least one of voice data of a care recipient who lies on the nursing bed, and image data obtained by imaging the care recipient;
bed posture information generating circuitry that generates bed posture mode information according to a demand by the care recipient based on the care recipient data; and
posture changing circuitry that changes the posture of the nursing bed based on the bed posture mode information,
wherein the bed posture information generating circuitry includes:
care recipient demand feature quantity extracting circuitry that extracts a demand feature quantity by which the care recipient's demand is characterized, from the care recipient data;
a memory that stores a plurality of kinds of demands of the care recipient, and the bed posture mode information for identifying the posture of the nursing bed associated with each of the plurality of kinds of demands; and
generating circuitry that reads the bed posture mode information associated with the care recipient's demand corresponding to the demand feature quantity extracted by the care recipient demand feature quantity extracting circuitry, from the memory,
wherein the bed posture information generating circuitry further includes demand identifying circuitry that identifies the care recipient's demand based on a given specific rule from the demand feature quantity,
wherein the care recipient data further includes time data indicative of time at which at least one of the voice data and the image data is generated, and
wherein the demand identifying circuitry identifies the care recipient's demand based on the demand feature quantity and the time data corresponding thereto.

2. The nursing bed posture changing device of claim 1, further comprising:
operational information acquiring circuitry that acquires operational information when the posture of the nursing bed is operated by a care worker corresponding to the care recipient's demand; and
bed posture mode information updating circuitry that updates the bed posture mode information stored in the memory so as to be associated with the demand, according to the operational information acquired by the operational information acquiring circuitry.

3. The nursing bed posture changing device of claim 1, wherein the bed posture information generating circuitry has a learned model learned with a large number of teaching data in which input data containing the care recipient data or processed data thereof is associated with output data containing bed posture mode information according to the care recipient's demand, and
wherein the bed posture information generating circuitry includes machine learning classifying circuitry that derives the output data corresponding to the input data to be recognized using the learned model.

4. The nursing bed posture changing device of claim 3, wherein the input data includes a demand feature quantity by which the care recipient's demand extracted from the care recipient data is characterized.

5. The nursing bed posture changing device of claim 4, further comprising:
teaching data acquiring circuitry that acquires the large number of teaching data, each comprised of a combination of input data containing the care recipient data or processed data thereof and output data containing bed posture mode information according to the care recipient's demand, the output data being a correct answer to the input data; and
machine learning circuitry that establishes the machine learning classifying circuitry that associates the input data with the output data by using the large number of teaching data.

6. A nursing bed system, comprising:
a nursing bed changeable of the shape of a floor of the bed, and/or a posture related to an angle of the entire bed; and
the nursing bed posture changing device of claim 1.

7. The nursing bed system of claim 6, further comprising at least one of a microphone that generates the voice data and a camera that generates the image data.

8. A nursing bed posture changing device that changes a posture of a nursing bed, the nursing bed being changeable of the shape of a floor of the bed, and/or a posture related to an angle of the entire bed, the device comprising:
means for acquiring care recipient data that acquires care recipient data containing at least one of voice data of a care recipient who lies on the nursing bed, and image data obtained by imaging the care recipient;
means for generating bed posture information that generates bed posture mode information according to a demand by the care recipient based on the care recipient data; and
means for changing posture that changes the posture of the nursing bed based on the bed posture mode information,
wherein the means for generating bed posture information includes:
means for extracting care recipient demand feature quantity that extracts a demand feature quantity by which the care recipient's demand is characterized, from the care recipient data;
a memory that stores a plurality of kinds of demands of the care recipient, and the bed posture mode information for identifying the posture of the nursing bed associated with each of the plurality of kinds of demands; and
means for reading that reads the bed posture mode information associated with the care recipient's demand corresponding to the demand feature quantity extracted by the means for extracting care recipient demand feature quantity, from the memory,
wherein the means for generating bed posture information further includes means for demand identifying that identifies the care recipient's demand based on a given specific rule from the demand feature quantity,
wherein the care recipient data further includes time data indicative of time at which at least one of the voice data and the image data is generated, and
wherein the means for demand identifying identifies the care recipient's demand based on the demand feature quantity and the time data corresponding thereto.

9. The nursing bed posture changing device of claim 8, further comprising:

means for acquiring operational information that acquires operational information when the posture of the nursing bed is operated by a care worker corresponding to the care recipient's demand; and that updates the bed posture mode information stored in the memory so as to be associated with the demand, according to the operational information acquired by the means for acquiring operational information.

10. The nursing bed posture changing device of claim 8, wherein the means for generating bed posture information has a learned model learned with a large number of teaching data in which input data containing the care recipient data or processed data thereof is associated with output data containing bed posture mode information according to the care recipient's demand, and wherein the means for generating bed posture information includes means for machine learning classifying that derives the output data corresponding to the input data to be recognized using the learned model.

11. The nursing bed posture changing device of claim 10, wherein the input data includes a demand feature quantity by which the care recipient's demand extracted from the care recipient data is characterized.

12. The nursing bed posture changing device of claim 11, further comprising:

means for acquiring teaching data that acquires the large number of teaching data, each comprised of a combination of input data containing the care recipient data or processed data thereof and output data containing bed posture mode information according to the care recipient's demand, the output data being a correct answer to the input data; and means for machine learning that establishes the means for machine learning classifying that associates the input data with the output data by using the large number of teaching data.

13. A nursing bed system, comprising:

a nursing bed changeable of the shape of a floor of the bed, and/or a posture related to an angle of the entire bed; and the nursing bed posture changing device of claim 8.

14. The nursing bed system of claim 13, further comprising at least one of a microphone that generates the voice data and a camera that generates the image data.

\* \* \* \* \*